US012087434B2

(12) United States Patent
Xu et al.

(10) Patent No.: US 12,087,434 B2
(45) Date of Patent: Sep. 10, 2024

(54) LOCATION-PROCEDURE EMBEDDING BASED METHOD FOR PATIENT IN-HOSPITAL LOCATION AND PROCEDURE PREDICTION

(71) Applicant: KONINKLIJKE PHILIPS N.V., Eindhoven (NL)

(72) Inventors: Liyi Xu, Cambridge, MA (US); Junzi Dong, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 833 days.

(21) Appl. No.: 16/868,597

(22) Filed: May 7, 2020

(65) Prior Publication Data
US 2020/0365257 A1 Nov. 19, 2020

Related U.S. Application Data

(60) Provisional application No. 62/846,895, filed on May 13, 2019.

(51) Int. Cl.
*G16H 40/20* (2018.01)
*G16H 10/60* (2018.01)
*G16H 15/00* (2018.01)
*G16H 50/20* (2018.01)
*G16H 50/70* (2018.01)

(52) U.S. Cl.
CPC ............ *G16H 40/20* (2018.01); *G16H 10/60* (2018.01); *G16H 15/00* (2018.01); *G16H 50/20* (2018.01); *G16H 50/70* (2018.01)

(58) Field of Classification Search
CPC ........ G16H 40/20; G16H 10/60; G16H 15/00; G16H 50/70; G16H 50/20
See application file for complete search history.

(56) References Cited

U.S. PATENT DOCUMENTS 10,839,950 B2 * 11/2020 Vaughan .............. A61B 5/7267
11,270,797 B1 * 3/2022 Shukla .................. G06F 16/242
(Continued)

OTHER PUBLICATIONS

"Using Tracking Tools to Improve Patient Flow in Hospitals". California Healthcare Foundation. Apr. 2011.

*Primary Examiner* — Jay M. Patel

(57) ABSTRACT

A method and system for predicting the next location for a patient in a healthcare facility, including: defining a location-procedure co-occurrence matrix for the healthcare facility, wherein the location-procedure co-occurrence matrix define the probability that a procedure will be performed in a specific location; defining a procedure transition matrix, wherein the procedure transition matrix defines the probability of moving from a first procedure to a second procedure; defining a patient input vector based upon the patient condition and procedures performed on the patient; calculating an output vector based upon the patient input vector and the procedure transition matrix; producing a procedure vector by setting all values in the output vector to zero except for the N highest values in the output vector, where N is an integer; calculating a location prediction vector based upon the procedure vector and the location-procedure co-occurrence matrix; and transmitting information regarding the M most likely next locations for the patient to a display device.

21 Claims, 4 Drawing Sheets

(56) References Cited

U.S. PATENT DOCUMENTS

| | | | |
|---|---|---|---|
| 2011/0295621 A1 | 12/2011 | Farooq et al. | |
| 2012/0065987 A1* | 3/2012 | Farooq | G16H 50/70 |
| | | | 705/2 |
| 2015/0080710 A1* | 3/2015 | Henkel | A61B 34/20 |
| | | | 600/407 |
| 2015/0213223 A1 | 7/2015 | Amarasingham et al. | |
| 2016/0029998 A1* | 2/2016 | Brister | A61B 8/0833 |
| | | | 600/424 |
| 2016/0378943 A1 | 12/2016 | Vallee | |
| 2017/0091410 A1 | 3/2017 | Averill et al. | |
| 2017/0140114 A1* | 5/2017 | Are | G06N 5/01 |
| 2018/0060492 A1* | 3/2018 | Feng | G16H 50/70 |
| 2018/0109936 A1 | 4/2018 | Mafera et al. | |
| 2018/0314793 A1* | 11/2018 | Gross | G16B 40/20 |
| 2018/0315502 A1* | 11/2018 | Wang | G16H 40/20 |
| 2018/0325407 A1* | 11/2018 | Varadan | A61B 5/339 |
| 2019/0043610 A1* | 2/2019 | Vaughan | A61B 5/4088 |
| 2019/0209022 A1* | 7/2019 | Sobol | A61B 5/02055 |
| 2020/0082941 A1* | 3/2020 | Wang | G16H 50/20 |
| 2020/0353271 A1* | 11/2020 | Dani | G16H 50/20 |

* cited by examiner

LOCATION-PROCEDURE EMBEDDING BASED METHOD FOR PATIENT IN-HOSPITAL LOCATION AND PROCEDURE PREDICTION

TECHNICAL FIELD

Various exemplary embodiments disclosed herein relate generally to a location-procedure embedding based method for patient in-hospital location & procedure prediction.

BACKGROUND

During hospital stays, patients are moved often for procedures, for surgery, due to deterioration, etc. On one hand, patients and families do not feel informed, and families are often surprised when patients are discharged or moved. In general, there is a lack of holistic view of a patient's in-hospital journey. Meanwhile, caregivers and hospital administrators do not have time in the middle of multiple clinical workflows to communicate with/inform patients and family with enough detail on what next step is and what possible outcomes are.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a method for predicting the next location for a patient in a healthcare facility, including: defining a location-procedure co-occurrence matrix for the healthcare facility, wherein the location-procedure co-occurrence matrix defines the probability that a procedure will be performed in a specific location; defining a procedure transition matrix, wherein the procedure transition matrix defines the probability of moving from a first procedure to a second procedure; defining a patient input vector based upon the patient condition and procedures performed on the patient; calculating an output vector based upon the patient input vector and the procedure transition matrix; producing a procedure vector by setting all values in the output vector to zero except for the N highest values in the output vector, where N is an integer; calculating a location prediction vector based upon the procedure vector and the location-procedure co-occurrence matrix; and transmitting information regarding the M most likely next locations for the patient to a display device.

Various embodiments are described, wherein the input vector is one-hot encoded.

Various embodiments are described, wherein producing a procedure vector further includes setting the N highest values in the output vector to one.

Various embodiments are described, further including determining the next most likely procedures for the patient.

Various embodiments are described, further comprising transmitting information regarding the next most likely procedures for the patient to a display device.

Various embodiments are described, wherein defining a location-procedure co-occurrence matrix includes collecting data for various procedures and their locations for a plurality of patients at the healthcare facility and analyzing the collected data to determine the probability that a specific procedure will occur in a specific location.

Various embodiments are described, wherein defining a procedure transition matrix includes collecting data for various procedures for a plurality number of patients at the healthcare facility and analyzing the collected data to determine the probability that a specific procedure will occur next after the procedure being analyzed.

Further various embodiments relate to a non-transitory machine-readable storage medium encoded with instructions for predicting the next location for a patient in a healthcare facility, including: instructions for defining a location-procedure co-occurrence matrix for the healthcare facility, wherein the location-procedure co-occurrence matrix defines the probability that a procedure will be performed in a specific location; instructions for defining a procedure transition matrix, wherein the procedure transition matrix defines the probability of moving from a first procedure to a second procedure; instructions for defining a patient input vector based upon the patient condition and procedures performed on the patient; instructions for calculating an output vector based upon the patient input vector and the procedure transition matrix; instructions for producing a procedure vector by setting all values in the output vector to zero except for the N highest values in the output vector, where N is an integer; instructions for calculating a location prediction vector based upon the procedure vector and the location-procedure co-occurrence matrix; and instructions for transmitting information regarding the M most likely next locations for the patient to a display device.

Various embodiments are described, wherein the input vector is one-hot encoded.

Various embodiments are described, wherein producing a procedure vector further includes setting the N highest values in the output vector to one.

Various embodiments are described, further comprising instructions for determining the next most likely procedures for the patient.

Various embodiments are described, further comprising instructions for transmitting information regarding the next most likely procedures for the patient to a display device.

Various embodiments are described, wherein instructions for defining a location-procedure co-occurrence matrix includes collecting data for various procedures and their locations for a plurality of patients at the health care facility and analyzing the collected data to determine the probability that a specific procedure will occur in a specific location.

Various embodiments are described, wherein instructions for defining a procedure transition matrix includes collecting data for various procedures for a plurality number of patients at the healthcare facility and analyzing the collected data to determine the probability that a specific procedure will occur next after the procedure being analyzed Further various embodiments relate to a system configured to predict the next location for a patient in a healthcare facility, including: a memory; a display; a processor coupled to the memory and the display, wherein the processor is configured to: define a location-procedure co-occurrence matrix for the healthcare facility, wherein the location-procedure co-occurrence matrix defines the probability that a procedure will be performed in a specific location; define a procedure transition matrix, wherein the procedure transition matrix defines the probability of moving from a first procedure to a second procedure; defining a patient input vector based upon the patient condition and procedures performed on the patient; calculate an output vector based upon the patient input vector and the procedure transition matrix; produce a procedure vector by setting all values in the output vector to zero except for the N highest values in the output vector, where N is an integer; calculate a location prediction vector based upon the procedure vector and the location-procedure co-occurrence matrix; and transmit information regarding the M most likely next locations for the patient to the display device.

Various embodiments are described, wherein the input vector is one-hot encoded.

Various embodiments are described, wherein producing a procedure vector further includes setting the N highest values in the output vector to one.

Various embodiments are described, wherein the processor is further configured to determine the next most likely procedures for the patient.

Various embodiments are described, wherein the processor is further configured to transmit information regarding the next most likely procedures for the patient to a display device.

Various embodiments are described, wherein defining a location-procedure co-occurrence matrix includes collecting data for various procedures and their locations for a plurality of patients at the health care facility and analyzing the collected data to determine the probability that a specific procedure will occur in a specific location.

Various embodiments are described, wherein defining a procedure transition matrix includes collecting data for various procedures for a plurality number of patients at the healthcare facility and analyzing the collected data to determine the probability that a specific procedure will occur next after the procedure being analyzed.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

During hospital stays, patients are moved often for procedures, for surgery, due to deterioration, etc. On one hand, patients and families do not feel informed, and families are often surprised when patients are discharged or moved. In general, there is a lack of holistic view of a patient's in-hospital journey. Meanwhile, caregivers and hospital administrators do not have time in the middle of multiple clinical workflows to communicate with/inform patients and family with enough detail on what next step is and what possible outcomes are.

An example of a patient's unit trace during a hospital stay may be: Clinical Decision Unit (CDU)→Emergency Room (ERH)→General Ward (4NE)→Medical intensive care unit (ICU) (5SE)→General Ward (4SW)→Post-anesthesia Care Unit (PACU)→General Ward (4NW).

Figure 1:
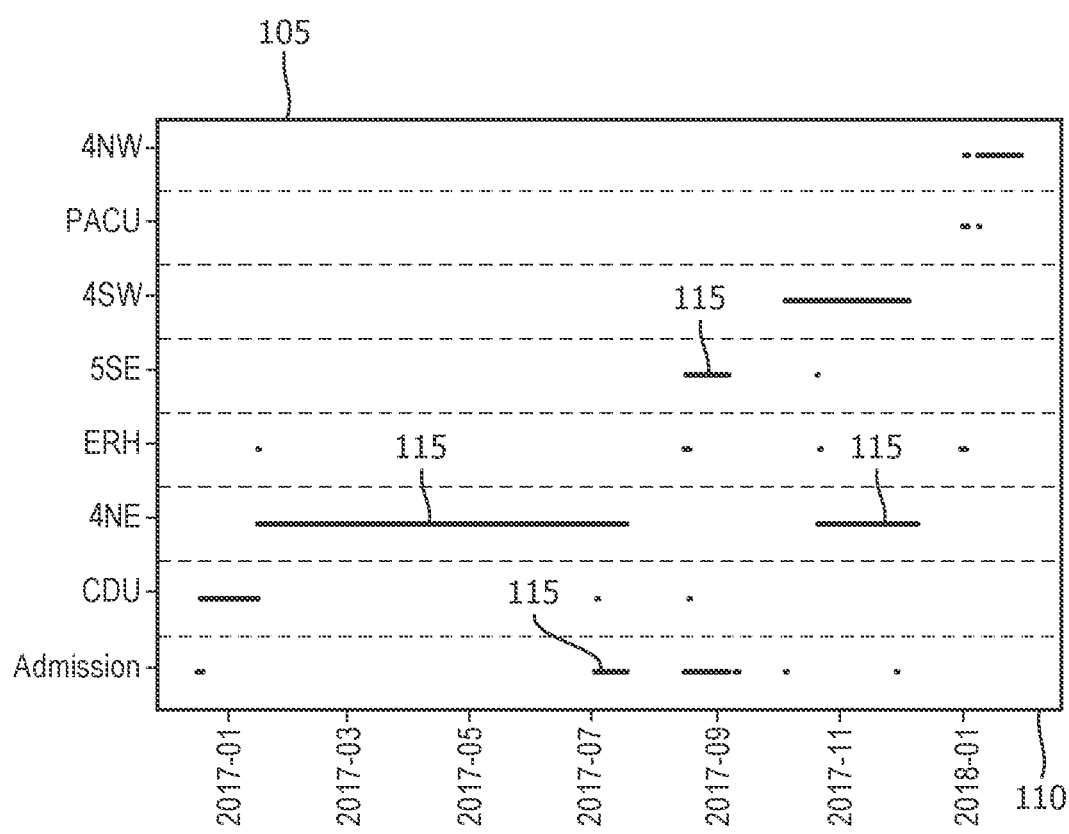
FIG. 1 illustrates the location of a specific patient over time.

In each unit, a patient might go through multiple procedures. Based on the patient's condition, multiple possibilities in terms of locations and procedures exist for the next step of their stay. For example, after coming into the emergency room, the patient may be sent for X-rays, to the general ward, or to the ICU. When a patient finishes having an X-ray, their next destination may be back to a room in the general ward or to another area of the hospital for another procedure such as an MRI. FIG. 1 illustrates the location of a specific patient over time. For example, the patient may visit the following areas over time that may include a single or multiple stays: general wards 4NW, 4SW, 5SE, and 4NE; PACU; EHR; CDU; and Admissions. These different areas are shown on the vertical axis 105. The horizontal axis 110 indicates the time frame that the patient was in the hospital. The horizontal traces 115 show the location of the patient in the different areas of the hospital during their stay(s). Overlaps occur, for example, when the patient is assigned to a room in the general ward, but then leaves for various procedures. The patient is still associated with the room in the general ward because that is where they will return after a procedure.

Currently, patients and families do not have information about these possibilities. Embodiments of a method and system that predicts a patient's next location and procedures for in-hospital care are described herein. The method and system produce a probability weighted outcome of a treatment pathway for the patient that may be presented to patients and their family and friends to enhance patients experience by aiding efficient communication and knowledge transfer between care-providers and patients. Such information may also be provided to caregivers as they work with patients as well. The system may present a user interface that may be used by the patient or their family and friends to understand where the patient currently is located, and what are the next possible locations and/or procedures that may be planned for the patient. Such a user interface may be available via various computer-based systems including computers, laptops, hospital work stations, tablets, smartphones, etc. Any device that could host and present the patient information may be used. Such devices may connect via the internet, local networks, cellular networks, etc. An example of such an interface will be given below.

Currently hospitals and other medical care facilities lack technologies that can provide in-hospital care location and procedures prediction for patients based on clinical workflow. Available technologies focus on predicting the occupancy rate of certain units/locations and overall for the hospitals. Sequential location prediction coupled with hierarchical relationship between procedures in different units have not been developed.

Current technologies are often payer and provider centric. Providing location and procedural predictions with a probability will help to improve patients experience and will keep family and patients informed by providing a view of their treatment and recovery journey.

An embodiment of a method and system for looking at and predicting the longitudinal relationship of patient location and procedure will now be described. This embodiment includes the following elements: 1) location-procedure embedding method; 2) location/procedure prediction; and 3) a new insight presented to patients and their family of the patient's journey with probability weighted outcomes for each clinical pivoting point.

Figure 2:
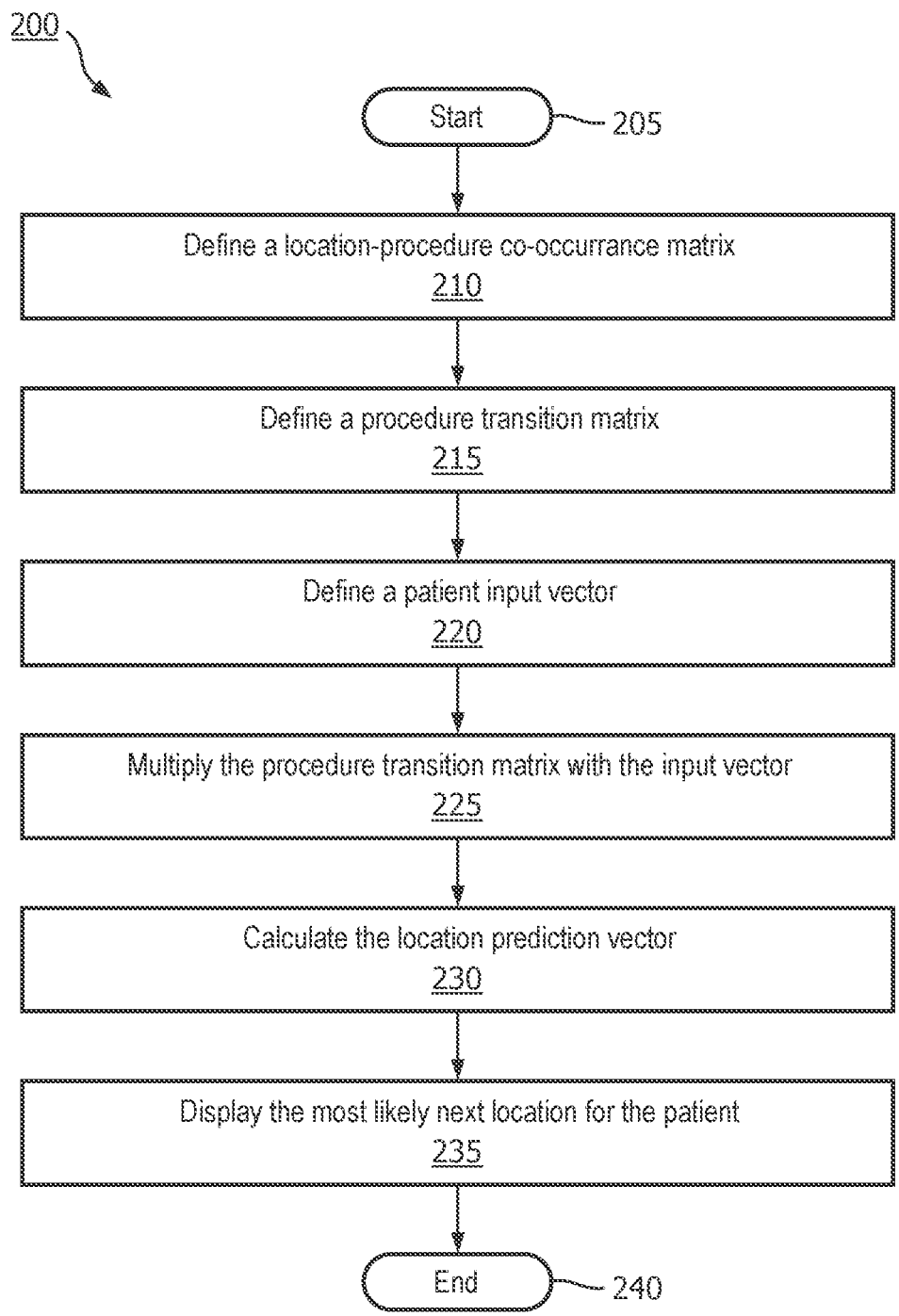
FIG. 2 illustrates a block diagram showing a method for predicting the longitudinal relationship of patient location and procedure.

FIG. 2 illustrates a block diagram showing a method for predicting the longitudinal relationship of patient location and procedure. The method starts at 205. Then, a location-procedure co-occurrence matrix X is defined 210 based on clinical guidelines and hospital workflow design that are common to tertiary care hospitals in the U.S. An example of such a location-procedure co-occurrence matrix X is given below. The matrix's rows are clinical procedures, e.g., ventilation, anesthesia, and pleurodesis, and the columns are standalone/unit locations corresponding to the clinical procedures, e.g., ICU and surgery room. For example, ventilation occurs in many locations, so $x_{1,j}$ has high probabilities in the ICU, PACU, and surgery room. On the other hand, pleurodesis (a lung surgical procedure) denoted by row m, is performed only in the surgery room, denoted by column n. Therefore, $x_{m,n}$ is the only value in row m, with a high probability value. The values for the location-procedure co-occurrence matrix X may be calculated by collecting data for various procedures and their locations for a large number of patients at a specific hospital. The data is then analyzed by location or procedure to determine the probability that a specific procedure will occur in a specific location. Such a location-procedure co-occurrence matrix X may be dependent upon the specific hospital and will be calculated for each hospital implementing the method predicting the longitudinal relationship of patient location and procedure. In other embodiments, where hospitals and care facilities are similar enough, the location-procedure co-occurrence matrix X, may be calculated for various similar facilities.

$$\begin{array}{c} \\ Ventilation \\ Anesthesia \\ \\ Pleurodesis \end{array} \begin{array}{cc} ICU & Surgery\ Room \\ \begin{bmatrix} x_{1,1} & \cdots & x_{1,j} & \cdots & x_{1,n} \\ \vdots & \ddots & \vdots & \ddots & \vdots \\ x_{i,1} & \cdots & x_{i,j} & \cdots & x_{i,n} \\ \vdots & \ddots & \vdots & \ddots & \vdots \\ x_{m,1} & \cdots & x_{m,j} & \cdots & x_{m,n} \end{bmatrix} \end{array}$$

Next, a procedure transition matrix P is defined 215 based on statistical analyses of specific clinical workflows. An example of the procedure transition matrix P is shown below. The rows and columns of the position transition matrix P are a comprehensive list of clinical procedures, for example ventilation, chest X-ray, anesthesia, and pleurodesis for a lung-related probability transition matrix. The probability of moving from procedure in the ith row to a procedure jth column is Pr(j|i). Similar to the location-procedure co-occurrence matrix X, the procedure transition matrix P may be calculated by collecting data for various procedures for a large number of patients at a specific hospital. The data is then analyzed by procedure to determine the probability that a specific procedure will occur next after the procedure being analyzed. Such a procedure transition matrix P may be dependent upon the specific hospital and will be calculated for each hospital implementing the method predicting the longitudinal relationship of patient location and procedure. In other embodiments, where hospitals and care facilities are similar enough, the procedure transition matrix P, may be calculated for various similar facilities. Further, the procedure transition matrix may be dependent upon certain conditions, so various procedure transition matrices may be developed for different diseases and conditions.

$$\begin{array}{c} \\ Ventilation \\ Chest\ X-ray \\ \\ Anethesia \\ \\ Pleurodesis \end{array} \begin{array}{c} Ventilation\ \ Chest\ X-ray\ \ Anethesia\ \ Pleurodes \\ \begin{pmatrix} P_{1,1} & P_{1,2} & \cdots & P_{1,j} & \cdots & P_{1,S} \\ P_{2,1} & P_{2,2} & \cdots & P_{2,j} & \cdots & P_{2,S} \\ \vdots & \vdots & \ddots & \vdots & \ddots & \vdots \\ P_{i,1} & P_{i,2} & \cdots & P_{i,j} & \cdots & P_{i,S} \\ \vdots & \vdots & \ddots & \vdots & \ddots & \vdots \\ P_{S,1} & P_{S,12} & \cdots & P_{S,j} & \cdots & P_{S,S} \end{pmatrix} \end{array}$$

As discussed above, both the transition matrix P and the co-occurrence matrix X may be calculated for a specific organization/hospital, but may be extended to a regional hospital network or extended nation-wide. This may occur when the variations among facilities are minimal.

Once a patient's first few procedures are recorded, an input vector with dimension (S,1) may be defined 220, which input vector has a length corresponding to all the clinical procedures (S) in the procedure transition matrix. A value of 1 is placed at each position in the input vector corresponding to a procedure, otherwise the other values of the vector are set to 0. An example of an input vector is shown below. In this case the patient has had ventilation performed and a chest X-ray performed.

$$\text{Input vector} = \begin{bmatrix} 1 \\ 1 \\ \vdots \\ 0 \\ \vdots \\ 0 \end{bmatrix} \begin{array}{l} Ventilation \\ Chest\ X-ray \\ \\ Anesthesia \\ \\ Pleurodesis \end{array}$$

Next, the procedure transition matrix P is multiplied with input vector 225 to obtain a (S,1) vector as the output vector. An example of an output vector is shown below. Next, the N procedures having the highest probability values may be selected. In this example N=5, but other values may be chosen up to the number of all of the different procedures.

$$\text{Output vector} = \begin{bmatrix} 0.3 \\ 0.1 \\ \vdots \\ 0.86 \\ \vdots \\ 0.6 \end{bmatrix} \begin{array}{l} Ventilation \\ Chest\ X-ray \\ \\ Anesthesia \\ \\ Pleurodesis \end{array}$$

Then the output vector may be one-hot encoded as shown below. In the example below for ease of illustrations, all 5 of the highest probability procedures are at the bottom of the output vector. Typically, these top 5 values would be spread throughout the output vector.

$$\text{Output vector} = \begin{bmatrix} 0.3 \\ 0.1 \\ \vdots \\ 0.86 \\ \vdots \\ 0.6 \end{bmatrix} \begin{matrix} \text{Ventilation} \\ \text{Chest X-ray} \\ \\ \text{Anesthesia} \\ \\ \text{Pleurodesis} \end{matrix} \Bigg\} \begin{matrix} \text{Top 5} \\ \text{probability} \end{matrix} \rightarrow \begin{matrix} \text{One-hot encoded} \\ \text{Procedure vector} \end{matrix} = \begin{bmatrix} 0 \\ 0 \\ \vdots \\ 1 \\ \vdots \\ 1 \end{bmatrix} \begin{matrix} \text{Ventilation} \\ \text{Chest X-ray} \\ \\ \text{Anesthesia} \\ \\ \text{Pleurodesis} \end{matrix}$$

The corresponding location prediction vector may then be calculated by multiplying $X^T$ by the one-hot encoded procedure vector 230 as shown below.

$$\begin{matrix} & \text{Ventilation} \quad \text{Anesthesia} \quad \text{Pleurodesis} \end{matrix}$$

$$\begin{matrix} ICU \\ \text{Pre-anethisia} \\ \text{care unit} \\ \text{Surgery} \\ \text{room} \end{matrix} \begin{bmatrix} x_{1,1} & \cdots & x_{1,j} & \cdots & x_{1,n} \\ \vdots & \ddots & \vdots & \ddots & \vdots \\ x_{i,1} & \cdots & x_{i,j} & \cdots & x_{i,n} \\ \vdots & \ddots & \vdots & \ddots & \vdots \\ x_{m,1} & \cdots & x_{m,j} & \cdots & x_{m,n} \end{bmatrix} \times$$

$$\begin{bmatrix} 0 \\ 0 \\ \vdots \\ 1 \\ \vdots \\ 1 \end{bmatrix} \begin{matrix} \text{Ventilation} \\ \text{Chest X-ray} \\ \\ \text{Anesthesia} \\ \\ \text{Pleurodesis} \end{matrix} = \begin{bmatrix} 0 \\ \vdots \\ 0.76 \\ \vdots \\ 0.72 \end{bmatrix} \begin{matrix} ICU \\ \\ \text{Pre-anthesthesia} \\ \text{care unit} \\ \\ \text{Surgeryroom} \end{matrix}$$

The location prediction vector has a number of values associated with each potential location in the hospital. The values are the probability that the patient's next location will be the specific location associated with that position in the location prediction vector. In the example above, based upon the patient's input vector, the probability that the patient's next location is the PACU is 0.76 and for the surgery room 0.72. At this point, a portion of these potential locations may be selected and presented to a user of the system/method 235. For example, the 5 locations having the highest probability may be selected and presented to the user. Alternatively, a threshold value may be set such that any location with a probability higher than say 0.5 will be selected and presented to the user. In yet another embodiment, both the threshold value and a number of locations may be used to select the locations to be present to the user, e.g., select all locations having a probability greater than 0.5 and then limit that number to 5 as needed.

Also, for each location, the most likely next procedure(s) may be determined based upon looking at the columns in the location-procedure co-occurrence matrix X associated with the most likely locations and selecting the procedure(s) with the highest probability at the specified locations.

Figure 3:
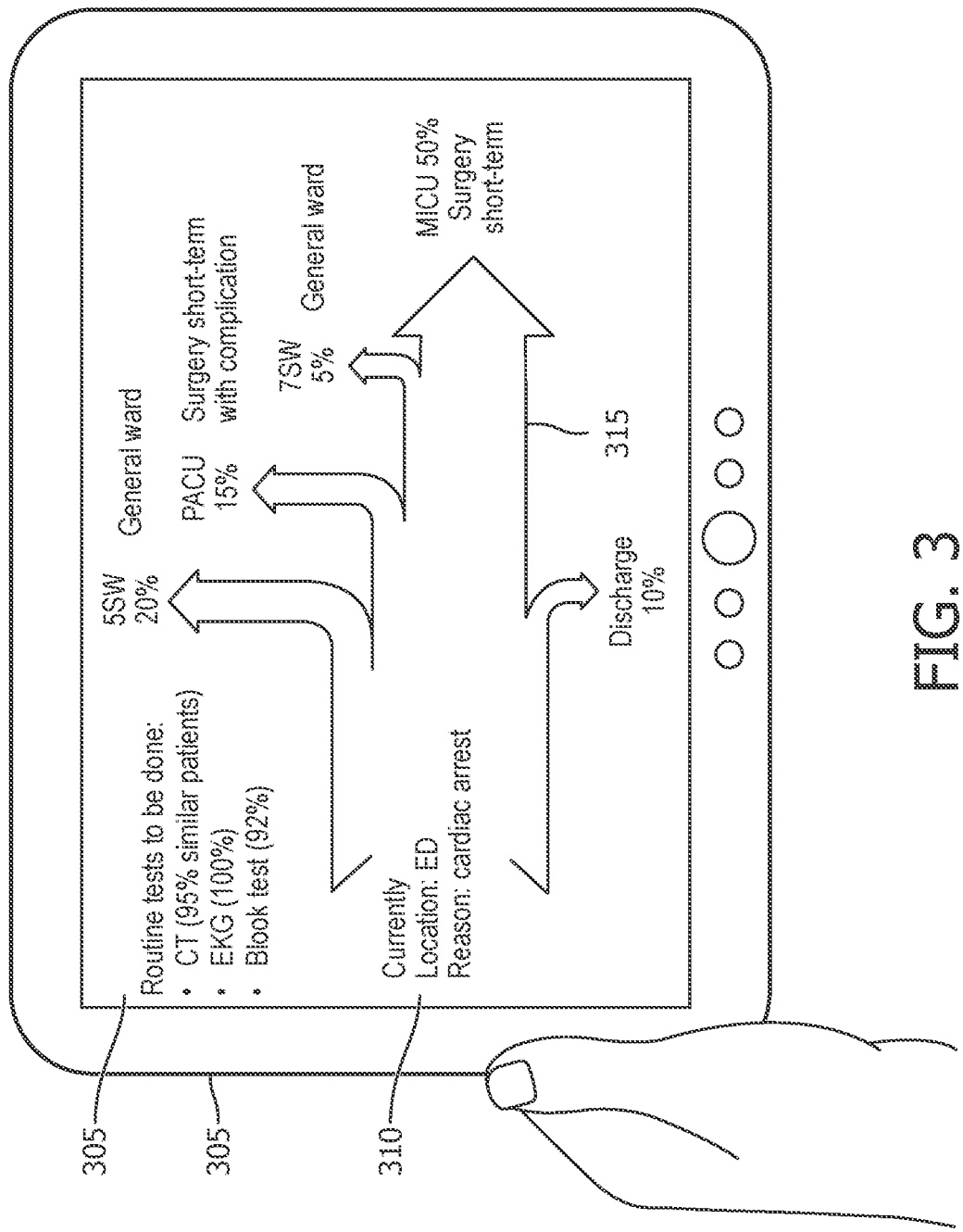
FIG. 3 illustrates one example of such a user interface implemented on a tablet computer.

Both the probability of the patient moving to a next location and the probability of the next procedure at that location may be presented to a user using a user interface. FIG. 3 illustrates one example of such a user interface implemented on a tablet computer. The tablet computer 305 may display various information relating to a patient. The routine tests 205 to be done may be listed and a percentage provided giving the probability that such a test will be applied to the patient in the near future. Also, the current location and reason that the patient is in that location may be shown 310. Then a graphic with arrows may be displayed that shows the next likely locations that the patient will next visit 315. Various locations are shown along with the probability that the patient will next move to that location. Such a display will provide information to the patient and their associated family and friends regarding the progress of their treatment and stay in the hospital. As a result, patients and their family and friends who subscribe to use the system will see probability weighted location and procedure prediction.

In an alternative embodiment, rather than one-hot encoding the output vector, only the top N probability values are kept, and the rest of the values are set to zero. This allows for the different procedures to be "weighted" differently from one another based upon their probability value, as opposed to the one-hot encoding that sets them all to 1 meaning they are have equal weight. In yet another embodiment, the output vector is not encoded at all and is multiplied with X to get the location prediction vector.

Figure 4:
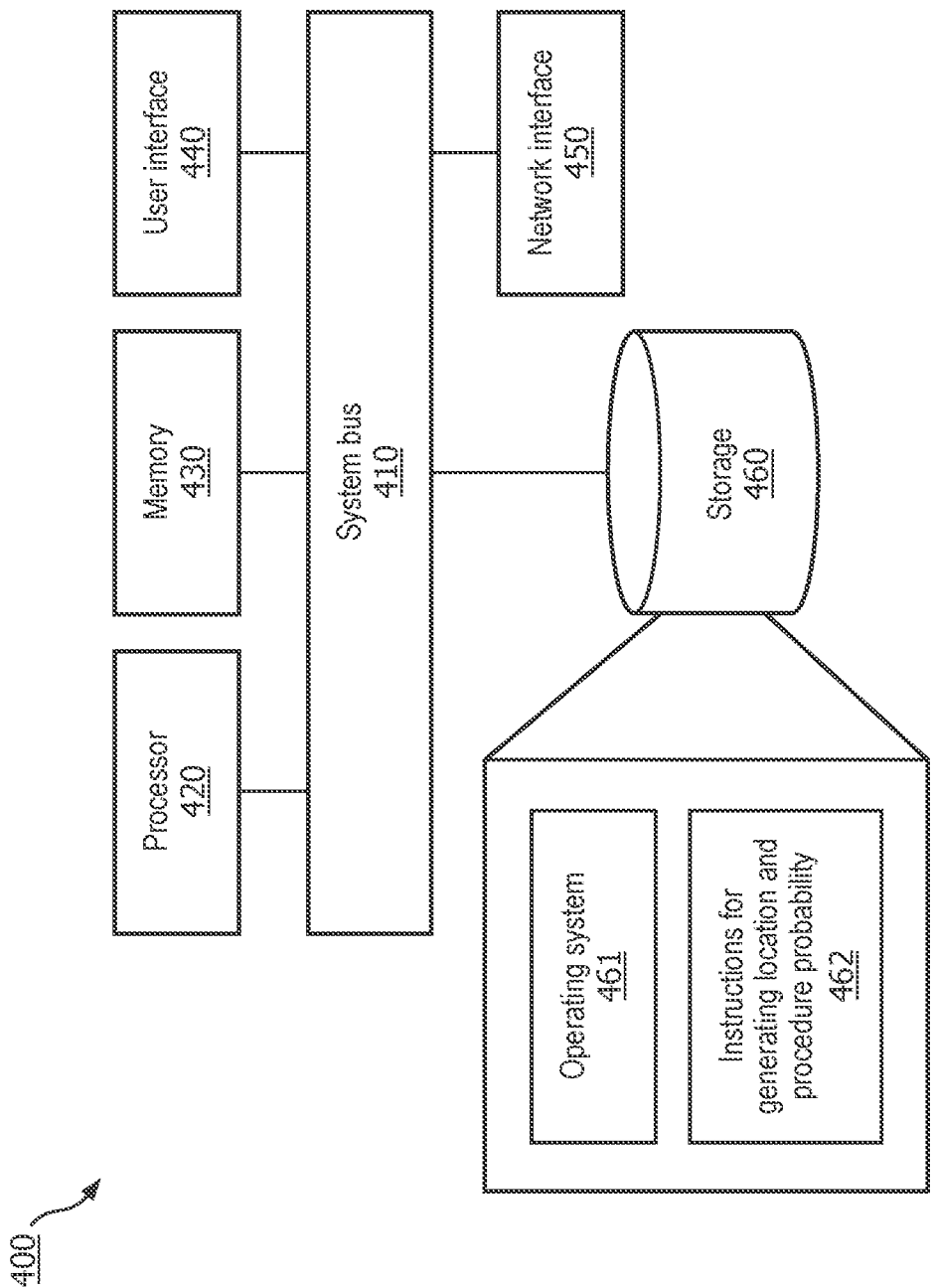
FIG. 4 illustrates an exemplary hardware diagram 400 for implementing the system and method described herein.

FIG. 4 illustrates an exemplary hardware diagram 400 for implementing the system and method described above. The exemplary hardware 400 may be the tablet 305 of FIG. 3 and implement the method of FIG. 2. As shown, the device 400 includes a processor 420, memory 430, user interface 440, network interface 450, and storage 460 interconnected via one or more system buses 410. It will be understood that FIG. 4 constitutes, in some respects, an abstraction and that the actual organization of the components of the device 400 may be more complex than illustrated.

The processor 420 may be any hardware device capable of executing instructions stored in memory 430 or storage 460 or otherwise processing data. As such, the processor may include a microprocessor, field programmable gate array (FPGA), application-specific integrated circuit (ASIC), or other similar devices.

The memory 430 may include various memories such as, for example L1, L2, or L3 cache or system memory. As such, the memory 430 may include static random-access memory (SRAM), dynamic RAM (DRAM), flash memory, read only memory (ROM), or other similar memory devices.

The user interface 440 may include one or more devices for enabling communication with a user such as a patient or family member or friend of the patient. For example, the user interface 440 may include a display, a touch interface, a mouse, and/or a keyboard for receiving user commands. In some embodiments, the user interface 440 may include a command line interface or graphical user interface that may be presented to a remote terminal via the network interface 450.

The network interface 450 may include one or more devices for enabling communication with other hardware devices. For example, the network interface 450 may include a network interface card (NIC) configured to communicate according to the Ethernet or other communications protocols, including wireless protocols. Additionally, the network interface 450 may implement a TCP/IP stack for communication according to the TCP/IP protocols. Various alternative or additional hardware or configurations for the network interface 450 will be apparent.

The storage 460 may include one or more machine-readable storage media such as read-only memory (ROM), random-access memory (RAM), magnetic disk storage media, optical storage media, flash-memory devices, or similar storage media. In various embodiments, the storage 460 may store instructions for execution by the processor 420 or data upon with the processor 420 may operate. For example, the storage 460 may store a base operating system 461 for controlling various basic operations of the hardware 400. The storage may also store instructions for carrying out the method of FIG. 2 and the other methods described above.

It will be apparent that various information described as stored in the storage 460 may be additionally or alternatively stored in the memory 430. In this respect, the memory 430 may also be considered to constitute a "storage device" and the storage 460 may be considered a "memory." Various other arrangements will be apparent. Further, the memory 430 and storage 460 may both be considered to be "non-transitory machine-readable media." As used herein, the term "non-transitory" will be understood to exclude transitory signals but to include all forms of storage, including both volatile and non-volatile memories.

While the host device 400 is shown as including one of each described component, the various components may be duplicated in various embodiments. For example, the processor 420 may include multiple microprocessors that are configured to independently execute the methods described herein or are configured to perform steps or subroutines of the methods described herein such that the multiple processors cooperate to achieve the functionality described herein.

The system and method described herein that helps to predict the next location and procedure for a patient solves the technological problem of helping a patient or the patient's family or friends know next potential location and procedure for the patient. Specifically, hospital and patient data is analyzed to determine the interaction between locations and procedures as well as order of procedures temporally. The system and method described above uses the collected and analyzed data to then predict for a particular patient what their next potential location and procedure might be along with their associated probabilities. This system and method is a practical application of various data processing techniques that results in providing specific and useful information about potential locations and procedures for the patient based upon the patient's prior treatments in the hospital. This practical application provides a technical advantage over other currently available systems that mostly focus on the utilization rate of certain locations in a hospital that do not provide any insight regarding a specific patient and their location and future procedures.

As described above, the embodiments described herein may be implemented as software running on a processor with an associated memory and storage. The processor may be any hardware device capable of executing instructions stored in memory or storage or otherwise processing data. As such, the processor may include a microprocessor, field programmable gate array (FPGA), application-specific integrated circuit (ASIC), graphics processing units (GPU), specialized neural network processors, cloud computing systems, or other similar devices.

The memory may include various memories such as, for example L1, L2, or L3 cache or system memory. As such, the memory may include static random-access memory (SRAM), dynamic RAM (DRAM), flash memory, read only memory (ROM), or other similar memory devices.

The storage may include one or more machine-readable storage media such as read-only memory (ROM), random-access memory (RAM), magnetic disk storage media, optical storage media, flash-memory devices, or similar storage media. In various embodiments, the storage may store instructions for execution by the processor or data upon with the processor may operate. This software may implement the various embodiments described above.

Further such embodiments may be implemented on multiprocessor computer systems, distributed computer systems, and cloud computing systems. For example, the embodiments may be implemented as software on a server, a specific computer, on a cloud computing, or other computing platform.

Any combination of specific software running on a processor to implement the embodiments of the invention, constitute a specific dedicated machine.

As used herein, the term "non-transitory machine-readable storage medium" will be understood to exclude a transitory propagation signal but to include all forms of volatile and non-volatile memory.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method for predicting a next location for a patient in a healthcare facility, comprising:
    defining a location-procedure co-occurrence matrix for the healthcare facility, wherein the location-procedure co-occurrence matrix defines the probability that a procedure will be performed in a specific location;
    defining a procedure transition matrix, wherein the procedure transition matrix defines the probability of moving from a first procedure to a second procedure;
    defining a patient input vector based upon a patient condition and one or more procedures performed on the patient;
    calculating an output vector based upon the patient input vector and the procedure transition matrix;
    producing a procedure vector by setting all values in the output vector to zero except for N highest values in the output vector, where N is an integer;
    calculating a location prediction vector based upon the procedure vector and the location-procedure co-occurrence matrix;
    transmitting information regarding M most likely next locations for the patient to a display device, wherein the M most likely next locations are selected based on a probability threshold and a threshold number of locations to be displayed on the display device;
    determining one or more next most likely procedures for the patient, wherein the transmitting further comprises transmitting information regarding the one or more next most likely procedures for the patient to the display device, and wherein the display device is a patient display device; and
    displaying, on the patient display device, the transmitted information regarding M most likely next locations for the patient, and the transmitted information regarding the one or more next most likely procedures for the patient, wherein the display comprises an arrow-based display, and further comprises:
        a display of a current location of the patient at a base of the arrow-based display;

a displayed list of the one or more next most likely procedures for the patient each with a determined probability of the procedure occurring; and a displayed diagram of the M most likely next locations for the patient, each comprising a determined probability of the location as a next destination for the patient, wherein each of the M most likely next locations for the patient are at a different end point of the arrow-based display.

2. The method of claim 1, wherein the input vector is one-hot encoded.

3. The method of claim 1, wherein producing a procedure vector further includes setting the N highest values in the output vector to one.

4. The method of claim 1, further including determining the next most likely procedures for the patient.

5. The method of claim 4, further comprising transmitting information regarding the next most likely procedures for the patient to a display device.

6. The method of claim 1, wherein defining a location-procedure co-occurrence matrix includes collecting data for various procedures and their locations for a plurality of patients at the healthcare facility and analyzing the collected data to determine the probability that a specific procedure will occur in a specific location.

7. The method of claim 1, wherein defining a procedure transition matrix includes collecting data for various procedures for a plurality number of patients at the healthcare facility and analyzing the collected data to determine the probability that a specific procedure will occur next after the procedure being analyzed.

8. A non-transitory machine-readable storage medium encoded with instructions for predicting a next location for a patient in a healthcare facility, comprising:
   instructions for defining a location-procedure co-occurrence matrix for the healthcare facility, wherein the location-procedure co-occurrence matrix defines the probability that a procedure will be performed in a specific location;
   instructions for defining a procedure transition matrix, wherein the procedure transition matrix defines the probability of moving from a first procedure to a second procedure;
   instructions for defining a patient input vector based upon a patient condition and one or more procedures performed on the patient;
   instructions for calculating an output vector based upon the patient input vector and the procedure transition matrix;
   instructions for producing a procedure vector by setting all values in the output vector to zero except for N highest values in the output vector, where N is an integer;
   instructions for calculating a location prediction vector based upon the procedure vector and the location-procedure co-occurrence matrix;
   instructions for transmitting information regarding M most likely next locations for the patient to a display device, wherein the M most likely next locations are selected based on a probability threshold and a threshold number of locations to be displayed on the display device;
   instructions for determining one or more next most likely procedures for the patient, wherein the transmitting further comprises transmitting information regarding the one or more next most likely procedures for the patient to the display device, and wherein the display device is a patient display device; and
   instructions for displaying, on the patient display device, the transmitted information regarding M most likely next locations for the patient, and the transmitted information regarding the one or more next most likely procedures for the patient, wherein the display comprises an arrow-based display, and further comprises:
      a display of a current location of the patient at a base of the arrow-based display;
      a displayed list of the one or more next most likely procedures for the patient each with a determined probability of the procedure occurring; and
      a displayed diagram of the M most likely next locations for the patient, each comprising a determined probability of the location as a next destination for the patient, wherein each of the M most likely next locations for the patient are at a different end point of the arrow-based display.

9. The non-transitory machine-readable storage medium of claim 8, wherein the input vector is one-hot encoded.

10. The non-transitory machine-readable storage medium of claim 8, wherein producing a procedure vector further includes setting the N highest values in the output vector to one.

11. The non-transitory machine-readable storage medium of claim 8, further comprising instructions for determining the next most likely procedures for the patient.

12. The non-transitory machine-readable storage medium of claim 11, further comprising instructions for transmitting information regarding the next most likely procedures for the patient to a display device.

13. The non-transitory machine-readable storage medium of claim 8, wherein instructions for defining a location-procedure co-occurrence matrix includes collecting data for various procedures and their locations for a plurality of patients at the health care facility and analyzing the collected data to determine the probability that a specific procedure will occur in a specific location.

14. The non-transitory machine-readable storage medium of claim 8, wherein instructions for defining a procedure transition matrix includes collecting data for various procedures for a plurality number of patients at the healthcare facility and analyzing the collected data to determine the probability that a specific procedure will occur next after the procedure being analyzed.

15. A system configured to predict the next location for a patient in a healthcare facility, comprising:
   a memory;
   a display device;
   a processor coupled to the memory and the display device, wherein the processor is configured to:
      define a location-procedure co-occurrence matrix for the healthcare facility, wherein the location-procedure co-occurrence matrix defines the probability that a procedure will be performed in a specific location;
      define a procedure transition matrix, wherein the procedure transition matrix defines the probability of moving from a first procedure to a second procedure;
      defining a patient input vector based upon a patient condition and one or more procedures performed on the patient;
      calculate an output vector based upon the patient input vector and the procedure transition matrix;

produce a procedure vector by setting all values in the output vector to zero except for N highest values in the output vector, where N is an integer;

calculate a location prediction vector based upon the procedure vector and the location-procedure co-occurrence matrix; and transmit information regarding M most likely next locations for the patient to the display device, wherein the M most likely next locations are selected based on a probability threshold and a threshold number of locations to be displayed on the display device;

determine one or more next most likely procedures for the patient, wherein the transmitting further comprises transmitting information regarding the one or more next most likely procedures for the patient to the display device, and wherein the display device is a patient display device; and display, on the patient display device, the transmitted information regarding M most likely next locations for the patient, and the transmitted information regarding the one or more next most likely procedures for the patient, wherein the display comprises an arrow-based display, and further comprises:
  a display of a current location of the patient at a base of the arrow-based display;
  a displayed list of the one or more next most likely procedures for the patient each with a determined probability of the procedure occurring; and
  a displayed diagram of the M most likely next locations for the patient, each comprising a determined probability of the location as a next destination for the patient, wherein each of the M most likely next locations for the patient are at a different end point of the arrow-based display.

16. The system of claim 15, wherein the input vector is one-hot encoded.

17. The system of claim 15, wherein producing a procedure vector further includes setting the N highest values in the output vector to one.

18. The system of claim 15, wherein the processor is further configured to determine the next most likely procedures for the patient, and further wherein the processor is configured to transmit information regarding the next most likely procedures for the patient to the display device.

19. The system of claim 15, wherein defining a location-procedure co-occurrence matrix includes collecting data for various procedures and their locations for a plurality of patients at the health care facility and analyzing the collected data to determine the probability that a specific procedure will occur in a specific location.

20. The system of claim 15, wherein defining a procedure transition matrix includes collecting data for various procedures for a plurality number of patients at the healthcare facility and analyzing the collected data to determine the probability that a specific procedure will occur next after the procedure being analyzed.

21. The method of claim 1, wherein one or more of the M most likely next locations for the patient, each at a different end point of the arrow-based display, comprises an arrow branching off from a main arrow.

* * * * *